United States Patent [19]

McColley

[11] Patent Number: Plant 5,355

[45] Date of Patent: Nov. 20, 1984

[54] PHILODENDRON PLANT

[76] Inventor: Cora McColley, P.O. Box 17126, Orlando, Fla. 32810

[21] Appl. No.: 467,439

[22] Filed: Feb. 17, 1983

[51] Int. Cl.[3] ..... A01H 5/12

[52] U.S. Cl. ..... Plt./88

[58] Field of Search ..... Plt./88

*Primary Examiner*—Robert E. Bagwill

*Attorney, Agent, or Firm*—Frank B. Robb

[57] ABSTRACT

A Philodendron plant of compact form having broad thick leathery leaves with prominent depressed veination, brick red color when immature and becoming black red upon maturing.

1 Drawing Figure

BACKGROUND AND DESCRIPTION OF THE INVENTION

The present invention comprises a new and distinct variety of Philodendron plant which is the result of selfing a seedling selected from crosses involving Philodendron wendlandii, hastatum, erubescens, imbe, fragrantissimum and an unnamed species.

An extensive program of hybridizing has been carried on in the vicinity of Orlando, Fla., much of the effort having been directed in an endeavor to develop a tough, leathery, Philodendron which is compact, an excellent keeper and as nearly black as possible. The Philodendron of the instant invention is that most nearly approaching the above objectives which has been developed to the present time, and of which I have knowledge, and I have therefore chosen to call it "Black Cardinal" for commercial identification.

The new variety has been asexually reproduced by single eye and tip cuttings in the vicinity of Orlando, Fla., and has been found to retain its distinctive characteristics through successive asexual reproduction.

The new variety has been exposed to adverse conditions in various areas, has provided superior foliage and thus is considered to be a superior foliage plant in every instance.

The new variety is distinctive from other Philodendron in cultivation and is not described by Graf, Bailey or Das Pflanzenreich. Perhaps the variety with which it may be most nearly compared is the Philodendron "Royal Queen" of U.S. Plant Pat. No. 3,396. While the variety of U.S. Plant Pat. No. 3,396 does produce almost black leaves, that color is more greyish brown and not the more red tone of the instant variety. There are other differences which are noted hereinafter and make the new variety distinctive, although it does show some of the elements of the plant patent referred to, that of "Royal Queen".

The new variety is visually distinguished by the following characteristics of the leaf, including an elliptic form with saggitate base and cuspidate leaf tip.

The leaves include pinnate veination, having smooth midribs and depressed veins.

An undulate surface prevails with the width of the leaves being about three-fourths of their length.

The plant itself is one which grows in very dense and compact, self-heading form, having alternate petioles which are from one-half to two-thirds the length of the leaf.

The petioles are semi-erect to erect, and the leaves horizontal to slightly erect with internodes ½" to 1".

Probably one of the most distinctive aspects of the new variety is that of the color of the leaves and the general impression created thereby, which leaves, petioles and stem are a black red, appearing almost black in medium to low light intensity. As the leaves mature after a period of six months for example, they turn to reddish-black green.

Certain of the physical characteristics of the plant of the new variety which are of value in the commercial field, include the fact that the plant will withstand extremely low light intensity and low soil moisture content for weeks. Actually a low humidity and high temperature are not particularly troublesome to the keeping of the plants under virtually all conditions. The leaves are very thick and leatherly and withstand bruising and dehydration without wilting.

The diseases to which the new variety is resistant include bacterial soft rot and it is almost immune to "shot gun" fungus.

The aspect of the plant in respect to growth which is noticeably different from others and in its mature form, is the very compact self-heading growth which does not require staking. The juvenile form of the plant is a stocky, compact-growing plant which makes an excellent free standing plant.

The growth of the plant indoors is not harmful, since it retains its desired form and size longer than other varieties known to be currently available.

Since the instant variety shares some of the characteristics of prior Philodendron varieties and specifically those of U.S. Plant Pat. No. 3,396, "Royal Queen", specific reference thereto is omitted and the details of the instant variety are emphasized in the following detailed specifications, based on observations made at Bamboo Nurseries, Inc. in the vicinity of Orlando, Fla.

The accompanying drawing forming a part of this disclosure, shows a typical plant of the new variety with the colors being as nearly true as possible in illustrating the variety hereof as made by photographic means.

The illustrations of the plant in the drawing are affected by the almost iridescent nature of the surfaces of those leaves which are highlighted. Thus the color references are in fact made to those leaves or portion of leaves which are in the shadow and thus the darkest areas in the drawing at the lower left, and at the lower right. The color reproduction herein is thus not entirely true when viewed as a whole but only at best helpful.

The shape and size of the leaves are proportional and correctly disclosed.

The general shape and leaf arrangement are obviously obscured. Thus the disclosure is at best a compromise since, when the plant is viewed directly and not through photography it presents a much darker appearance, the brownish edges and reddish reverse of the central leaf of the drawing being much more subdued.

The leaf petioles are in fact as black as those disclosed in most of the plant as shown.

Color references are made to the Munsell Color Cascade published by MacBeth Kolmorgen Corporation, with observations being recorded by daylight illumination under vinyl of not more than 30% shade.

FORM CHARACTERISTICS

Leaf shape:

a. *Mature.*—Elliptic.

b. *Immature.*—Elliptic to ovate.

c. *Tip.*—Cuspidate.

d. *Base.*—(1.) Mature: Sagittate. (2.) Immature: Sagittate.

e. *Displacement.*—Undulate.

f. *Margin.*—Entire.

g. *Veination.*—Smooth midrib, sunken veins.

Leaf attachment: Stalked.

Leaf arrangement: Alternate; slightly vertical to horizontal.

Petiole: Medium; horizontal to semi-erect.

Stem: Short; heavy internodes ½" to 1".

Overall appearances: Open, self-heading, free standing.

SIZE CHARACTERISTICS OF TYPICAL COMMERCIAL SIZE

Leaf itself:

a. *Width-widest point.*—12¾".

b. *Width-1" from top.*—3".

c. *Length.*—17½".

d. *Thickness.*—0.018.

Petiole:

a. *Length.*—10"-13".

b. *Diameter (center).*—½" to ¾".

c. *Internode spacing.*—½" to 1".

d. *Stem diameter.*—1178 "-2".

COLOR CHARACTERISTICS

Leaf (mature):

a. *Top.*—29-16 (Estimated).

b. *Bottom.*—29-15.

Leaf (immature):

a. *Top.*—35-16 (Estimated).

b. *Bottom.*—33-16 (Estimated).

Leaf veination:

a. *Midrib.*—29-15.

b. *Veins.*—26-16 (Estimated).

Stem, (darker): 41-16 (Estimated).

Petiole, (darker): 40-16 (Estimated).

I claim:

1. A new and distinct variety of Philodendron plant, substantially as herein disclosed, characterized as to novelty by compact plant form, broad, thick, leathery leaves having depressed veination, brick red leaf color when immature, black red color when fully mature, ability to withstand low light intensity and low soil moisture content for long periods of time.

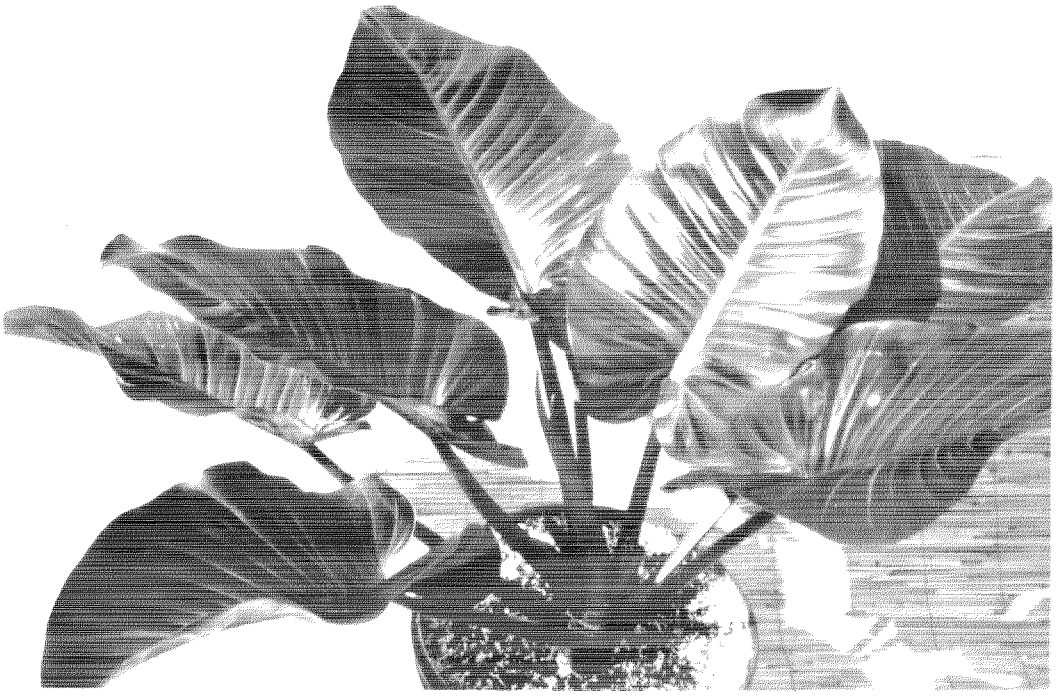

* * * * *